(12) United States Patent
Weber

(10) Patent No.: US 11,008,266 B2
(45) Date of Patent: May 18, 2021

(54) AROMATIZATION PROCESS USING HEAVY AROMATIC CIRCULATION

(71) Applicant: Chevron Phillips Chemical Company LP, The Woodlands, TX (US)

(72) Inventor: Eric P. Weber, Kingwood, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 0 days.

(21) Appl. No.: 16/564,314

(22) Filed: Sep. 9, 2019

(65) Prior Publication Data

US 2020/0002250 A1  Jan. 2, 2020

Related U.S. Application Data

(62) Division of application No. 15/952,575, filed on Apr. 13, 2018, now Pat. No. 10,487,026.

(51) Int. Cl.
| | |
|---|---|
| *B01J 19/24* | (2006.01) |
| *C07C 5/41* | (2006.01) |
| *C07C 5/31* | (2006.01) |

(52) U.S. Cl.
CPC .............. *C07C 5/417* (2013.01); *B01J 19/24* (2013.01); *C07C 5/31* (2013.01); *C07C 5/415* (2013.01); *B01J 2219/00103* (2013.01); *B01J 2219/24* (2013.01)

(58) Field of Classification Search
CPC . C07C 5/417; C07C 5/415; C07C 5/31; B01J 19/24; B01J 2219/24; B01J 2219/00103
USPC ........................................................ 422/187
See application file for complete search history.

(56) References Cited

U.S. PATENT DOCUMENTS

| | | | |
|---|---|---|---|
| 1,122,435 A | * | 12/1914 | Erratum ............... A01K 31/002 217/59 |
| 2,882,244 A | | 4/1959 | Milton |
| 3,002,036 A | | 9/1961 | Hieronymus |
| 3,130,007 A | | 4/1964 | Breck |
| 3,216,789 A | | 11/1965 | Breck et al. |
| 4,021,447 A | | 5/1977 | Rubin et al. |
| 4,162,214 A | | 7/1979 | Maslyansky et al. |

(Continued)

FOREIGN PATENT DOCUMENTS

GB    1542774 A    3/1979

*Primary Examiner* — Huy Tram Nguyen
(74) *Attorney, Agent, or Firm* — Eversheds Sutherland (US) LLP

(57) ABSTRACT

Disclosed are a catalytic method and system for producing aromatic hydrocarbons from aliphatic hydrocarbons or light naphtha. In an aspect, the process comprises adding a diluent comprising a heavy aromatic hydrocarbon (for example, $C_7$-$C_{9+}$) to a reactor feedstock comprising aliphatic hydrocarbons (for example, $C_6$-$C_8$) or light naphtha to form a reactor feed stream, such that the heat capacity of reactor feed stream is higher than the heat capacity of feedstock. The reactor feed stream is heated and contacting with a catalyst under conditions sufficient to aromatize at least a portion of the aliphatic hydrocarbons and form a product stream comprising a primary aromatic hydrocarbon product and a heavy aromatic hydrocarbon product. In an aspect, the diluent can comprise a heavy aromatic hydrocarbon having at least one carbon atom more than the primary aromatic hydrocarbon product.

20 Claims, 1 Drawing Sheet

(56) References Cited

U.S. PATENT DOCUMENTS

| | | | |
|---|---|---|---|
| 4,503,023 A | | 3/1985 | Breck et al. |
| 4,642,402 A | * | 2/1987 | Jensen .................. C07C 2/76 585/411 |
| 5,013,423 A | | 5/1991 | Chen et al. |
| 5,203,988 A | | 4/1993 | Swan, III et al. |
| 5,401,386 A | | 3/1995 | Morrison et al. |
| 5,675,054 A | * | 10/1997 | Manley ................. B01D 3/146 203/71 |
| 5,877,367 A | | 3/1999 | Witte |
| 6,004,452 A | | 12/1999 | Ash et al. |
| 6,190,539 B1 | | 2/2001 | Holtermann et al. |
| 6,323,381 B1 | | 11/2001 | Nacamuli et al. |
| 6,812,180 B2 | | 11/2004 | Fukunaga |
| 7,153,801 B2 | | 12/2006 | Wu |
| 7,563,358 B2 | | 7/2009 | Stavens et al. |
| 7,932,425 B2 | | 4/2011 | Blessing et al. |
| 2015/0224464 A1 | | 8/2015 | Grott et al. |
| 2016/0083313 A1 | * | 3/2016 | Negiz .................... C07C 15/00 585/313 |

* cited by examiner

US 11,008,266 B2

AROMATIZATION PROCESS USING HEAVY AROMATIC CIRCULATION

CROSS-REFERENCE TO RELATED APPLICATIONS

This application is a division of U.S. patent application Ser. No. 15/952,575, filed on Apr. 13, 2019, the entirety of which is incorporated herein by reference.

TECHNICAL FIELD

The present disclosure is directed to a method and system for producing aromatic hydrocarbons.

BACKGROUND

Aliphatic hydrocarbons, such as those produced from petroleum distillates and biomass, are frequently used in aromatization processes, to catalytically convert these aliphatic hydrocarbons to aromatic hydrocarbons, which are commercially valuable chemical products.

To improve the conversion of aliphatic hydrocarbons to aromatic hydrocarbons, additional heat must typically be supplied, for example through the use of a recycled hydrogen diluent stream. However, hydrogen has a very low heat capacity, and the use of hydrogen recycle inhibits progress of the forward reaction of aliphatic hydrocarbons to aromatic hydrocarbons. Therefore, there remain significant challenges to producing aromatic hydrocarbons.

SUMMARY

Aromatization is the process for catalytic conversion of aliphatic hydrocarbons, such as those found in a naphtha stream, to aromatic hydrocarbons, containing ring structures. Aromatization refers not to one but several reactions that take place simultaneously. These reactions include removal of hydrogen from cycloalkanes and alkyl-cycloalkanes, removal of hydrogen from and isomerization of alkyl-cycloalkanes, and removal of hydrogen from and cyclization of aliphatic hydrocarbons. Outside of these reactions, side reactions can occur, including dealkylation of alkylbenzenes, isomerization of aliphatic hydrocarbons, and hydrocracking reactions which produce light gaseous hydrocarbons such as methane, ethane, propane and butane.

These aromatic hydrocarbons, especially benzene, are valued as chemical precursors to polymer products, but they can also be valuable as solvents and as fuel or fuel additives due to their high octane number. Given their commercial importance, an ongoing need exists for improved systems and processes designed to maximize the production of these aromatic hydrocarbons from sustainable or renewable materials.

In one aspect, this disclosure provides a system and method for producing aromatic hydrocarbons from a reactor feedstock comprising aliphatic hydrocarbons using a diluent comprising a heavy aromatic hydrocarbon having at least one carbon atom more than the primary aromatic hydrocarbon product.

In another aspect, this disclosure provides a process for producing aromatic hydrocarbons comprising: adding a diluent comprising a heavy aromatic hydrocarbon to a reactor feedstock comprising aliphatic hydrocarbons or light naphtha to form a reactant feed stream at a first temperature; heating the reactant feed stream in a furnace to a second temperature; contacting the heated reactant feed stream with a catalyst comprising an inorganic support, a Group 8-10 metal, and halide under conditions for aromatizing at least a portion of the aliphatic hydrocarbons, thereby forming a product or reactor effluent stream at a third temperature, the reactor effluent stream comprising a primary aromatic hydrocarbon product and a heavy aromatic hydrocarbon product; separating the reactor effluent stream into the primary aromatic hydrocarbon product, the heavy aromatic hydrocarbon product, hydrogen, and a raffinate; and forming a diluent from the heavy aromatic hydrocarbon product; wherein forming the diluent comprises adding the heavy aromatic hydrocarbon having at least one carbon atom more than the primary aromatic hydrocarbon product.

In a further aspect, this disclosure provides a catalytic hydrocarbon reforming system comprising: a fractionator having an inlet to receive an initial feedstock comprising naphtha and an outlet to discharge a reactor feedstock comprising aliphatic hydrocarbons or light naphtha; a diluent input line for adding a diluent comprising a heavy aromatic hydrocarbon to the reactor feedstock to form a reactant feed stream having a first temperature; a furnace capable of heating the reactant feed stream to a second temperature; at least one reactor charged with a catalyst comprising an inorganic support, a Group 8-10 metal, and at least one halide, the reactor having an inlet to receive the reactant feed stream and an outlet to discharge a product or reactor effluent stream at a third temperature, the reactor effluent stream comprising a primary aromatic hydrocarbon product and a heavy aromatic hydrocarbon product; a separation system that receives the reactor effluent stream and separately discharges the primary aromatic hydrocarbon product, the heavy aromatic hydrocarbon product, hydrogen, and a raffinate; a first return line extending from the separation system to the diluent input line for providing the diluent, the diluent comprising at least a portion of the heavy aromatic hydrocarbon product; separating the reactor effluent stream into the primary aromatic hydrocarbon product, the heavy aromatic hydrocarbon product, hydrogen, and a raffinate; and forming the diluent from the heavy aromatic hydrocarbon product; and wherein forming the diluent comprises adding the heavy aromatic hydrocarbon having at least one carbon atom more than the primary aromatic hydrocarbon product.

These and other aspects, embodiments and features are discussed in detail in the detailed description, the appended claims and the figures provided in this disclosure.

DETAILED DESCRIPTION

Definitions

Figure 1:
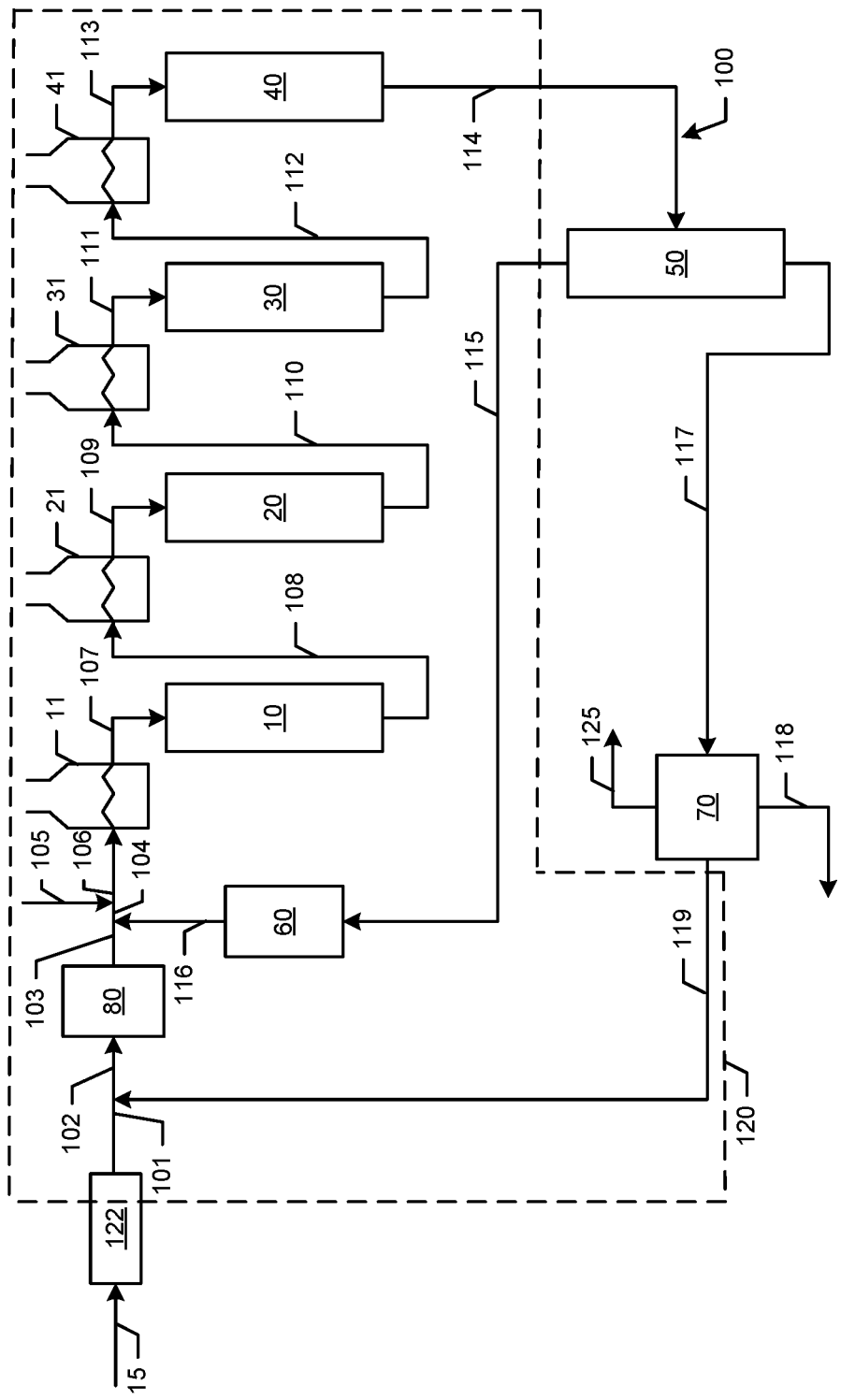
FIG. 1 presents a schematic diagram of an aspect of an aromatization reactor system for producing aromatic hydrocarbons according to an embodiment of the present disclosure.

Certain terms are used throughout the following description and claims to refer to particular features or components. As one skilled in the art will appreciate, different persons can refer to the same feature or component by different names. This document does not intend to exhaustively distinguish between components or features that differ in name but not structure or function.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

In the following discussion and in the claims, the terms "includes," "is," "containing," "having," "characterized by," and "comprises" are used in an open-ended fashion, and thus should be interpreted to mean "including, but not limited to." When systems and methods are claimed or described in terms of "comprising" various components or steps, the systems and methods can also "consist essentially of" or "consist of" the various components or steps, unless stated otherwise.

The terms "a," "an," and "the" are intended to include plural alternatives, e.g., at least one. For instance, the disclosure of "a feedstock," "a compound," "a catalyst," and the like, is meant to encompass one, or mixtures or combinations of more than one feedstock, compound, catalyst, and the like, unless otherwise specified.

Various numerical ranges can be disclosed herein. When Applicant discloses or claims a range of any type, Applicant's intent is to disclose or claim individually each possible number that such a range could reasonably encompass, including end points of the range as well as any sub-ranges and combinations of sub-ranges encompassed therein, unless otherwise specified. Moreover, all numerical end points of ranges disclosed herein are approximate. As a representative example, Applicants disclose, in an aspect of the invention, that one or more steps in the processes disclosed herein can be conducted at a temperature in a range from 65° C. to 75° C. This range should be interpreted as encompassing temperatures in a range from "about" 65° C. to "about" 75° C., and further encompass each of 65° C., 66° C., 67° C., 68° C., 69° C., 70° C., 71° C., 72° C., 73° C., 74° C., and 75° C., including any ranges and sub-ranges between any of these values.

Applicants reserve the right to proviso out or exclude any individual members of any such group, including any sub-ranges or combinations of sub-ranges within the group, that can be claimed according to a range or in any similar manner, if for any reason Applicants choose to claim less than the full measure of the disclosure, for example, to account for a reference that Applicants can be unaware of at the time of the filing of the application. Further, Applicants reserve the right to proviso out or exclude any individual substituents, groups, analogs, compounds, ligands, structures, pressures, temperatures, and the like, or any members of a claimed genus or subgenus, if for any reason Applicants choose to claim less than the full measure of the disclosure, for example, to account for a reference that Applicants can be unaware of at the time of the filing of the application.

All publications and patents mentioned herein are incorporated herein by reference for the purpose of describing and disclosing, for example, the constructs and methodologies that are described in the publications, which might be used in connection with the presently described invention. The publications discussed throughout the text are provided solely for their disclosure prior to the filing date of the present application. Nothing herein is to be construed as an admission that the inventors are not entitled to antedate such disclosure by virtue of prior invention.

The following discussion is directed to various aspects or embodiments of the invention. The figures are not necessarily to scale, therefore, certain features of the embodiments can be shown exaggerated in scale or in somewhat schematic form and some details of conventional elements may not be shown in the interest of clarity and conciseness. Although one or more of these embodiments can be preferred, the embodiments disclosed should not be interpreted, or otherwise used, as limiting the scope of the disclosure, including the claims. It is to be fully recognized that the different teachings of the embodiments discussed below can be employed separately or in any suitable combination to produce desired results. In addition, one skilled in the art will understand that the following description has broad application, and the discussion of any embodiment is meant only to be exemplary of that embodiment, and not intended to intimate that the scope of the disclosure, including the claims, is limited to that embodiment.

As used herein, "about" can be used to account for variations due to experimental error. All numerical measurements are understood to be modified by the word "about", whether or not "about" is explicitly recited, unless specifically stated otherwise. Thus, for example, the statement "production of 10,000 tonnes," is understood to mean "production of about 10,000 tonnes." In some aspects, the term "about" is used to specify that the value can vary by ±2% of the recited value, ±5% of the recited value, or ±10% of the recited value.

Generally, groups of elements are indicated using the numbering scheme indicated in the version of the periodic table of elements published in Chemical and Engineering News, 63(5), 27, 1985. In some instances, a group of elements can be indicated using a common name assigned to the group; for example, alkali metals for Group 1 elements, alkaline earth metals for Group 2 elements, transition metals for Group 3-12 elements, halogens or halides for Group 17 elements, and the like.

For any particular compound or group disclosed herein, any name or structure (general or specific) presented is intended to encompass all conformational isomers, regioisomers, stereoisomers, and mixtures thereof that can arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to hexane includes hexane, 2-methylpentane, 3-methylpentane, 2,2-dimethylbutane, and 2,3-dimethyl-butane; and a general reference to a butyl group includes an n-butyl group, a sec-butyl group, an iso-butyl group, and a t-butyl group.

In one aspect, a chemical "group" can be defined or described according to how that group is formally derived from a reference or "parent" compound, for example, by the number of hydrogen atoms removed from the parent compound to generate the group, even if that group is not literally synthesized in such a manner. These groups can be utilized as substituents or coordinated or bonded to metal atoms. By way of example, an "alkyl group" formally can be derived by removing one hydrogen atom from an alkane. The disclosure that a substituent, ligand, or other chemical moiety can constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

As used herein, the term "hydrocarbon" refers to a compound containing only carbon and hydrogen atoms. Other identifiers can be utilized to indicate the presence of particular groups, if any, in the hydrocarbon (e.g., halogenated hydrocarbon indicates the presence of one or more halogen atoms replacing an equivalent number of hydrogen atoms in the hydrocarbon).

An "aliphatic" compound or "aliphatic hydrocarbon" is defined according to the IUPAC recommended definition to mean an acyclic or cyclic, saturated or unsaturated carbon compound, excluding aromatic compounds. That is, an aliphatic compound is a non-aromatic organic compound.

An "aromatic" compound or "aromatic hydrocarbon" is a compound containing a cyclically conjugated double bond system that follows the Hückel (4n+2) rule and contains (4n+2) pi-electrons, where n is an integer from 1 to 5. Aromatic hydrocarbons include "arenes" (aromatic compounds, e.g., benzene, toluene, and xylenes) and "heteroarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2)). As disclosed herein, the term "substituted" can be used to describe an aromatic group, arene, or heteroarene, wherein a non-hydrogen moiety formally replaces a hydrogen atom in the compound, and is intended to be non-limiting, unless specified otherwise.

As used herein, the term "heavy aromatic hydrocarbon" refers to an aromatic hydrocarbon having at least seven hydrocarbon products. For example, $C_7$-$C_{12}$ aromatic hydrocarbon compounds are heavy aromatic hydrocarbons.

As used herein, the term "alkane" refers to a saturated hydrocarbon compound. Other identifiers can be utilized to indicate the presence of particular groups, if any, in the alkane (e.g., halogenated alkane indicates the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. The alkane or alkyl group can be linear or branched unless otherwise specified.

A "cycloalkane" is used herein to refer to a saturated cyclic hydrocarbon, with or without side chains, for example, cyclobutane, cyclopentane, cyclohexane, methyl cyclopentane, and methyl cyclohexane. Other identifiers can be utilized to indicate the presence of particular groups, if any, in the cycloalkane (e.g., halogenated cycloalkane indicates the presence of one or more halogen atoms replacing an equivalent number of hydrogen atoms in the cycloalkane).

As used herein, a "paraffin" refers to a non-cyclic, linear or branched saturated hydrocarbon. For example, a $C_6$ paraffin is a non-cyclic, linear or branched hydrocarbon having 6 carbon atoms per molecule. Normal hexane, methylpentanes, dimethylbutanes are examples of $C_6$ paraffins. A paraffin-containing feed comprises non-cyclic saturated hydrocarbons, such as normal paraffins, isoparaffins, and mixtures thereof.

As used herein, a "naphthene" and "naphthenic" are terms used to describe cycloalkanes and their alkyl derivatives, that is, their alkyl-substituted analogs. Therefore, a "naphthene" is a cyclic, saturated hydrocarbon having one or more rings of carbon atoms in its chemical structure and is used herein to mean the same as "cycloalkane." If such a cyclic structure includes unsaturated carbon-carbon bonds but is not aromatic, such compounds would be aliphatic, but not naphthenic. In some embodiments, a naphthene is a cyclic, saturated hydrocarbon having from 5 to 8 carbon atoms in the cyclic structure, including substituted (particularly alkyl-substituted) analogs thereof.

As used herein, "naphtha" is a petroleum distillate fraction boiling within the temperature range of from 50° F. to 550° F. (10° C. to 288° C.). In some embodiments, naphtha boils within the temperature range of 70° F. to 450° F. (21° C. to 232° C.), and more typically within the range of 80° F. to 400° F. (27° C. to 204° C.), and often within the range of 90° F. to 360° F. (32° C. to 182° C.). In some embodiments, at least 85 vol. % (volume percent) of naphtha boils within the temperature range of from 50° F. to 550° F. (10° C. to 288° C.), and more typically within the range of from 70° F. to 450° F. (21° C. to 232° C.). In embodiments, at least 85 vol. % of naphtha is in the $C_4$-$C_{12}$ range, and more typically in the $C_5$-$C_{11}$ range, and often in the $C_6$-$C_{10}$ range. Naphtha can include, for example, straight run naphthas, paraffinic raffinates from aromatic extraction or adsorption, $C_6$-$C_{10}$ paraffin containing feeds, bio-derived naphtha, naphtha from hydrocarbon synthesis processes, including Fischer Tropsch and methanol synthesis processes, as well as naphtha from other refinery processes, such as hydrocracking or conventional reforming. The term "light naphtha" is generally used herein to refer to a petroleum distillate fraction boiling in the temperature range of from about 68° F. (20° C.) to about 455° F. (235° C.).

As used herein, the term "convertible hydrocarbon", "convertible C6 species" or "convertible C7 species" refers to a hydrocarbon compound which is readily reacted to form aromatic hydrocarbons under aromatization process conditions. While a "non-convertible hydrocarbon" is a highly-branched hydrocarbon that is not readily reacted to form aromatic hydrocarbons under aromatization process conditions. For example, a "non-convertible hydrocarbon" can comprise highly-branched hydrocarbons having six or seven carbon atoms with an internal quaternary carbon or hydrocarbons having six carbons atoms and two adjacent internal tertiary carbons or mixtures thereof. A "convertible C6" is hydrocarbon containing six carbons without an internal quaternary carbon or two adjacent internal tertiary carbons, for example, hexane, 2-methyl-pentane, 3-methyl-pentane, cyclohexane, and methyl cyclopentane. A "convertible C7" is hydrocarbon containing seven carbons without an internal quaternary carbon, for example, n-heptane, 2-methylhexane, 3-methylhexane, 2,3-dimethylpentane, 2,4-dimethylpentane, methyl cyclohexane, dimethyl cyclopentane. The "non-convertible hydrocarbons," that is, the highly branched hydrocarbons with six or seven carbon atoms and an internal quaternary carbon, can comprise, for example, 2,2-dimethylbutane, 2,2-dimethylpentane, 3,3-dimethylpentane, and 2,2,3-trimethylbutane. The highly branched hydrocarbons with six carbon atoms and adjacent internal tertiary carbons can comprise, for example, 2,3-dimethylbutane. The non-convertible highly branched hydrocarbons do not easily convert to aromatic hydrocarbons and instead tend to convert to light hydrocarbons under aromatization process conditions.

As used herein "primary aromatic hydrocarbon," "primary aromatic product," "desired hydrocarbon product," and "particular aromatic species" are used interchangeably and refer to the aromatic hydrocarbon that is the desired end product of the reaction and comprises aromatic hydrocarbon that has been generated from a feed that includes a renewable cellulose source. For example, the desired product can be benzene and toluene can be a by-product, or the desired product can be toluene and xylene can be a by-product.

A "Group 8-10" metal includes each of the Group 8 metals iron, ruthenium, and osmium, each of the Group 9 metals cobalt, rhodium, and iridium, and each of the Group 10 metals nickel, palladium, and platinum. The Group 8-10 metals can also be referred to using the earlier nomenclature, the Group VIII metals, which also encompasses all of iron, ruthenium, osmium, cobalt, rhodium, iridium, nickel, palladium, and platinum. The term "platinum metals" is used according to the understanding of the person of ordinary skill to refer to the second and third row metals of Groups 8-10, specifically, ruthenium, osmium, rhodium, iridium, palladium, and platinum, which can also be referred to as the noble Group 8 metals. Generally, describing the catalyst as a Group 8-10 metal catalyst or as comprising a Group 8-10 metal, is intended to encompass catalysts that include at least one Group 8-10 metal and optionally other metals, such as Pt/Sn and Pt/Re.

As used herein the term "catalytic reactor system" and "reactor system" when referring to aromatization reactor systems also refer to the reactor vessel, reactor internals, and associated processing equipment as the context allows, including but not limited to the catalyst, inert packing materials, scallops, flow distributors, center pipes, reactor ports, catalyst transfer and distribution system, furnaces and other heating devices, heat transfer equipment, and piping. The catalytic reactor system described can comprise a fixed catalyst bed system, a moving catalyst bed system, a fluidized catalyst bed system, or combinations thereof. Such reactor systems can be batch or continuous. In a fixed bed system, the flow of the feed can be upward, downward, or radially through the reactor.

The term "halogen" has its usual meaning and, as the context allows, includes halides. Therefore, examples of halogens include fluorine, fluoride, chlorine, chloride, bromine, bromide, iodine, and iodide.

Molar selectivities are defined as follows:

Benzene selectivity: $S_{Bz} = \frac{\dot{n}_{Bz,prod}}{\dot{n}_{conv\,C6,feed} - \dot{n}_{conv\,C6,prod}}$  Eq. 1

Toluene selectivity: $S_{Tol} = \frac{\dot{n}_{Tol,prod}}{\dot{n}_{conv\,C7,feed} - \dot{n}_{conv\,C7,prod}}$  Eq. 2

Benzene + Toluene selectivity: $S_{Bz+Tol} =$  Eq. 3
$\frac{\dot{n}_{Bz,prod} + \dot{n}_{Tol,prod}}{\dot{n}_{conv\,C6,C7,feed} - \dot{n}_{conv\,C6,C7,prod}}$ Aromatics selectivity: $S_{arom} = \frac{\dot{n}_{Bz,prod} + \dot{n}_{Tol,prod} + \dot{n}_{C8+arom,prod}}{\dot{n}_{conv\,C6-C8+,feed} - \dot{n}_{conv\,C6-C8+,prod}}$  Eq. 4

Conversion is defined as the number of moles converted per mole of "convertible" hydrocarbons fed as follows:

C6 conversion: $X_{C6} = \frac{\dot{n}_{conv\,C6,feed} - \dot{n}_{conv\,C6,prod}}{\dot{n}_{conv\,C6,feed}}$  Eq. 5

C7 conversion: $X_{C7} = \frac{\dot{n}_{conv\,C7,feed} - \dot{n}_{conv\,C7,prod}}{\dot{n}_{conv\,C7,feed}}$  Eq. 6

C6 + C7 conversion: $X_{C6+C7} =$  Eq. 7
$\frac{\dot{n}_{conv\,C6,feed} + \dot{n}_{conv\,C7,feed} - \dot{n}_{conv\,C6,prod} - \dot{n}_{conv\,C7,prod}}{\dot{n}_{conv\,C6,feed} + \dot{n}_{conv\,C7,feed}}$ In these equations, $\dot{n}$ indicates a molar flow rate in a continuous reactor or the number of moles in a batch reactor.

A "tonne" is used herein to refer to a metric ton, that is, a unit of mass equal to 1,000 kilograms.

DESCRIPTION

This disclosure provides a system and method for producing aromatic hydrocarbons from aliphatic hydrocarbons, using a diluent comprising a recycled aromatic hydrocarbon product. Using hydrogen diluents, the dehydration of aliphatic hydrocarbons to produce aromatic hydrocarbons, such as the dehydrogenation of hexane to produce benzene, results in a high yield of aromatic hydrocarbons, for example of yields of greater than 80%. These dehydrogenation reactions are highly endothermic, so the dehydrogenation of aliphatic hydrocarbons to produce aromatic hydrocarbons typically occurs in a series of reactors where heat is added between each reactor to maintain the reactants at the desired temperatures and further drive conversion of reactants to products. However, this disclosure provides the benefits of at least the ability to add less heat between reactors and increase the conversion rate compared to traditional hydrogen diluent systems, by using a diluent stream comprising a heavy aromatic hydrocarbon, which has a higher heat capacity than hydrogen.

Generally, the feedstock for the aromatization process is naphtha, a petroleum distillate which can be generated from oil wells, natural condensates, or other suitable sources. The naphtha feedstock can comprise a light hydrocarbon, with a boiling range of about 20° C. to about 235° C. The naphtha feed can contain aliphatic, naphthenic, or paraffinic hydrocarbons. While catalytic aromatization typically refers to the conversion of naphtha, other feedstocks also can be treated to provide product enriched in aromatic hydrocarbons. Therefore, in one aspect while the conversion of hexane in the presence of naphtha is described, the present disclosure can be useful for the conversion or aromatization of hexane with other feedstocks such as paraffin hydrocarbons, olefin hydrocarbons, acetylene hydrocarbons, cyclic paraffin hydrocarbons, cyclic olefin hydrocarbons, and mixtures thereof, and particularly saturated hydrocarbons. The particular aromatic hydrocarbons that are produced in the aromatization reactor(s) is dependent on the composition of the feedstock.

Typically, the initial naphtha feedstock is fed into a purification process or purification module which is part of the aromatization reactor. The purification process employs known methods to purify the hydrocarbon feed, which can include fractionation, purification, and/or treating of the hydrocarbon feed. Fractionation can include removing heavy (e.g., $C_{9+}$ ($C_9$ or greater)) hydrocarbons and/or light (e.g., $C_{5-}$ ($C_5$ or less)) hydrocarbons, and treating refers interchangeably to removing impurities, such as oxygenates, sulfur, and/or metals, from the hydrocarbon feed. The resulting purified stream, generally contains compounds with about 6 to about 9 carbon atoms, for example, about 6 to about 8 carbon atoms. Typically, for the production of a benzene product, the feedstock will have more $C_6$ compounds than $C_7/C_8$ compounds, and generally will have substantially more $C_6$ compounds than $C_7$ or $C_8$ compounds. By "substantially" more, it is intended to reflect, for example, a 1.5-fold to 25-fold excess of $C_6$ compounds over $C_7/C_8$ compounds, or alternatively, a 2-fold to 15-fold excess of $C_6$ compounds over $C_7/C_8$ compounds, or alternatively, a 5-fold to 10-fold excess of $C_6$ compounds over $C_7/C_8$ compounds. In any case, mixtures of aromatic compounds including benzene, toluene, and xylenes can be produced from available feedstocks.

The Reactor System and Process

FIG. 1 illustrates an exemplary catalytic reactor system 100 for the production of aromatic hydrocarbons from feedstock 101. This catalytic reactor system 100 comprises four catalytic reforming reactors 10, 20, 30, and 40 in series, each of which has a reactor feed 107, 109, 111, and 113 and a reactor effluent 108, 110, 112, and 114, respectively. Each reactor feed 107, 109, 111, and 113 is heated by furnaces 11, 21, 31, and 41, respectively. The fourth reactor effluent 114 is fed to a hydrogen separation process 50 which separates the fourth reactor effluent 114 into hydrogen stream 115 and reformate stream 117. Hydrogen stream 115 can be fed to dryer 60 to form dried hydrogen stream 116, which can be recycled through catalytic reactor system 100. Reformate 117 can be fed to purification-extraction process 70, where it is separated into raffinate stream 125, recycle stream 119, and primary product stream 118.

As shown in FIG. 1, catalytic reactor system 100 comprises four catalytic reforming reactors in series, designated as reactors 10, 20, 30, and 40. However, catalytic reactor system 100 can comprise any suitable number and configuration of aromatization reactors, for example one, two, three, five, six, or more reactors in series and/or in parallel. Reactors 10, 20, 30, and 40 can be of any suitable type, including but not limited to radial flow reactors, plug flow reactors, packed bed reactors, fluidized bed reactors, continuously stirred reactors (CSTR), and the like. FIG. 1 illustrates reactor feedstock 101 being combined with recycle stream 119 comprising a heavy aromatic hydrocarbon, before it is fed via combined stream 102 to purification process 80. In some embodiments, feedstock 101 can comprise any suitable reactants, such as $C_6$ to $C_8$ aliphatic hydrocarbons and naphtha, light naphtha, or combinations thereof. In some embodiments, feedstock 101 can further comprise a stabilizer selected from one or more $C_7$-$C_{10}$ paraffins. In some embodiments, the heavy aromatic hydrocarbon can comprise an aromatic hydrocarbon with at least one carbon atom more than the primary aromatic hydrocarbon product 118. Purification process 80 purifies combined stream 102, for example, by removing impurities to create purified stream 103, the composition of which forms the basis for the type of aromatic hydrocarbons being produced. In some embodiments, purification process 80 can further include a sulfur removal system. In some embodiments, purification process 80 can further include a sulfur converter-absorber. In some embodiments, catalytic reactor system 100 can further comprise fractionator 122 located upstream of feedstock 101. In these embodiments, the fractionator receives an input of initial feedstock 15 which comprises naphtha, and discharges feedstock 101, which comprises aliphatic hydrocarbons and/or light naphtha.

Aromatization reactions are highly endothermic, consuming more heat than they produce. Recycle stream 119 can act as a diluent heat source, which distributes heat loss over a greater amount of material, allowing for maintaining a more consistent temperature in the reactor. Specifically, the recycled heavy aromatic hydrocarbons included in recycle stream 119 can act as a more efficient diluent heat source than hydrogen, due to their relatively higher heat capacities. Additionally, unlike hydrogen, heavy aromatic hydrocarbons will have no effect on the forward progress of the aromatization reaction. Specifically, because the heavy aromatic hydrocarbons are not a product of the desired aromatization reaction, they will not affect the equilibrium of the desired reaction. In some embodiments, recycle stream 119 can comprise toluene, xylenes, $C_{9+}$ aromatic hydrocarbon compounds, hydrogen, or combinations thereof. In some embodiments, recycle stream 119 can comprise toluene and xylenes. In some embodiments, recycle stream 119 can comprise toluene, xylenes, and $C_{9+}$ aromatic compounds.

Thus, without intending to be bound by theory, using recycle stream 119 comprising heavy aromatic hydrocarbons either alone or in combination with hydrogen stream 115 as a diluent heat source can lead to less inter-reactor heat needed from furnaces 11, 21, 31, 41, and can also lead to higher conversion rates compared to aromatization reactor systems which only use hydrogen as a diluent heat source. Similarly, without intending to be bound by theory, using recycle stream 119 comprising heavy aromatic hydrocarbons either alone or in combination with a stream of dried hydrogen 125 as a diluent heat source can allow the temperatures of first reactor feed 107, second reactor feed 109, third reactor feed 111, and fourth reactor feed 113 to be lower than the temperatures of these feed streams when using only hydrogen as a diluent heat source. Further, without intending to be bound by theory, using the recycle stream 119 comprising heavy aromatic hydrocarbons either alone or in combination with hydrogen stream 115 as a diluent heat source can result in a smaller temperature drop across each of reactors 10, 20, 30, and 40 than when hydrogen is used alone as a diluent heat source. In other words, the difference in temperatures between each of first reactor feed 107 and first reactor effluent 108, second reactor feed 109 and second reactor effluent 110, third reactor feed 111 and third reactor effluent 112, and fourth reactor feed 113 and fourth reactor effluent 114, can be smaller when recycle stream 119 comprising heavy aromatic hydrocarbons is used either alone or in combination with hydrogen stream 115 than when hydrogen is used alone as a diluent heat source. Further, if the temperatures and/or temperature drops in the furnaces are reduced, this can subsequently reduce the heat duty that must be provided by the furnaces, wherein the heat duty is typically obtained by the combustion of fuel gas. This can result in significant cost savings to the operator, and can result in higher conversion rates, since the reactants will be more likely to remain within the desired temperature range throughout the length of the reactor.

In an embodiment, the catalytic reactor system as described in FIG. 1. can achieve an overall conversion of at least about 60% on a molar basis. In another embodiment, the overall conversion can be greater than about 60%, 65%, 70%, 75%, 80%, 85%, 90%, 95%, 97%, 98%, 99%, 99.9%, or 99.99% on a molar basis. In another embodiment, the overall conversion can be greater than about 60% but less than 100% on a molar basis. In another embodiment, the conversion is equal to or greater than about 80%, 81%, 82%, 83%, 84%, or 85%. It is understood by one of ordinary skill in the art that conversion cannot exceed 100%.

Feed stream 104 can be fed to reactor 100 or can further be combined with oxygenate and/or nitrogenate stream 105 to produce reactor feed stream 106. An oxygenate stream, a nitrogenate stream, or mixtures thereof can be inserted into the aromatization system at various times, in various locations, and in various manners, as discussed herein. Oxygenate and/or nitrogenate addition causes a specific amount of water and/or ammonia to be present in one or more aromatization reactors during the aromatization process. The presence of a specific amount of water and/or ammonia in an aromatization reactor can activate or enhance the aromatization catalyst.

As aromatization reactions are highly endothermic, large temperature drops can occur across the reactors. Therefore, each reactor 10, 20, 30, and 40 in the series can comprise a corresponding furnace 11, 21, 31, and 41, respectively, for preheating components to a desired temperature or maintaining a desired reaction rate. Alternatively, one or more reactors can share a common furnace where practical. According to an aspect, catalytic reactor system 100 (e.g., reactors 10, 20, 30, and 40; furnaces 11, 21, 31, and 41; hydrogen separation process 50; dryer 60; purification-extraction process 70; and purification process 80; valves; pumps; etc.) can be coupled to a computer system that can communicate with one or more components of catalytic reactor system 100 so as to set or adjust operating parameters.

Traditional aromatization reactions are commonly run in a series of adiabatic reactors, i.e., reactors in which no heat enters the reactor save the input streams. As the reaction proceeds through the reactors, the average heat in the reactor vessels will decline. Since catalyst activity decreases at lower temperature, and catalyst deactivation increases at higher temperature, there is a balance between how hot the input stream temperature can be and how low the output temperature can be to achieve optimal catalytic activity. Optimal temperature ranges differ depending upon the catalyst and the aromatization process being carried out. The use of a diluent heat source allows more time to be spent reacting at the optimal temperature. As an alternative to an adiabatic reactor, aromatization reactions can be carried out in an isothermal reactor, i.e., one in which the temperature remains constant.

Reactor feed stream 106 can be pre-heated in a first furnace 11, which heats the hydrocarbons to a desired temperature, thereby producing first reactor feed 107. First reactor feed 107 can be fed into reactor 10, where the hydrocarbons are contacted with an aromatization catalyst under suitable reaction conditions (e.g., temperature and pressure) for aromatizing one or more components in the feed to increase the aromatic hydrocarbon content thereof.

First reactor effluent 108 comprises aromatic hydrocarbons, unreacted feed, and other hydrocarbon compounds or by-products. First reactor effluent 108 can be sent to hydrogen separator 50 or can be pre-heated in second furnace 21. Second furnace 21 reheats the hydrocarbons to a desired temperature thereby producing second reactor feed 109. Second reactor feed 109 can be then fed into reactor 20, where the hydrocarbons are contacted with an aromatization catalyst under suitable reaction conditions for aromatizing one or more components in the feed to increase the aromatic hydrocarbon content thereof. Second reactor effluent 110 comprising aromatic hydrocarbons, unreacted feed, and other hydrocarbon compounds or by-products is recovered from second reactor 20.

Second reactor effluent 110 can be sent to hydrogen separator 50 or pre-heated in third furnace 31, which again reheats the hydrocarbons to a desired temperature, thereby producing third reactor feed 111. Third reactor feed 111 can be then fed into reactor 30, where the hydrocarbons are contacted with an aromatization catalyst under suitable reaction conditions for aromatizing one or more components in the feed to increase the aromatic hydrocarbon content thereof. Third reactor effluent 112 comprising aromatic hydrocarbons, unreacted feed, and other hydrocarbon compounds or by-products is recovered from third reactor 30.

Third reactor effluent 112 can be sent to hydrogen separator 50, for example, or can be pre-heated in fourth furnace 41, which again reheats the hydrocarbons to a desired temperature, thereby producing fourth reactor feed 113. Fourth reactor feed 113 can be then fed into reactor 40, where the hydrocarbons are contacted with an aromatization catalyst under suitable reaction conditions for aromatizing one or more components in the feed to increase the aromatic hydrocarbon content thereof. Fourth reactor effluent 114 comprising aromatic hydrocarbons, unreacted feed, and other hydrocarbon compounds or by-products is recovered from fourth reactor 40.

Fourth reactor effluent 114 is then fed into hydrogen separation process 50, although a portion of the fourth reactor effluent 114 can be directed into further downstream reactors for additional conversion. Methods to separate hydrogen stream 115 from reformate 117 are well known. According to one embodiment, hydrogen stream 115 is not recycled and is instead sent to downstream processes, such as downstream reactors for additional conversion. According to another embodiment, at least a portion of hydrogen stream 115 is recycled, where it can be added, for example to purified feed stream 103 to form a component of reactor feed stream 104. In some embodiments, hydrogen stream 115 can be recycled and added to the purified stream 103 via a third return line. In some embodiments, this third return line can first provide hydrogen stream 115 to dryer 60 to provide dried hydrogen stream 116, wherein dried hydrogen stream 116 is then added to purified stream 103.

Reformate 117 can comprise aromatization reaction products from reactors 10, 20, 30, and 40 (e.g., primary aromatic hydrocarbon product, heavy aromatic hydrocarbon product, and non-aromatic hydrocarbons) in addition to any unreacted feed and other hydrocarbon compounds or by-products.

In some embodiments, oxygenate and/or nitrogenate can be added at alternative locations within reaction zone 120 to increase/maintain catalyst activity. Oxygenates, nitrogenates, or mixtures thereof described herein can be used alone, in combination, or further combined to produce other suitable oxygenates or nitrogenates. In some embodiments, the oxygenate and nitrogenate can be contained within the same bifunctional compound. The oxygenate and/or nitrogenate can be added in any suitable physical phase such as a gas, liquid, or combinations thereof.

The oxygenate and/or nitrogenate can be added to one or more process streams and/or components via any suitable means for their addition, for example a pump, injector, sparger, bubbler, or the like. The oxygenate and/or nitrogenate can be introduced as a blend with a carrier. In some embodiments, the carrier can be hydrogen, a hydrocarbon, nitrogen, an inert gas, or mixtures thereof. In a preferred embodiment, the carrier is hydrogen.

The oxygenate and/or nitrogenate can be added at various locations within the aromatization system described herein. For example, the oxygenate and/or nitrogenate can be added to one or more process streams in catalytic reactor system 100, to one or more equipment components or vessels of catalytic reactor system 100, or combinations thereof. In an embodiment, the oxygenate and/or nitrogenate can be added at one or more locations within a reaction zone defined by reactor system 100, wherein the reaction zone comprises process flow lines, equipment, and/or vessels wherein reactants are undergoing an aromatization reaction.

In one embodiment, oxygenate and/or nitrogenate stream 105 is added between purification process 80 and first furnace 11, as shown in FIG. 1. Alternatively, the oxygenate and/or nitrogenate stream can be added within purification process 80. However, it is also contemplated that the oxygenate and/or nitrogenate stream can be added at various other locations within catalytic reactor system 100. For example, the oxygenate and/or nitrogenate stream can be added to the initial feedstock 15, the feed 101, the combined feed 102, the first reactor feed 107, the first reactor effluent 108, the second reactor feed 109, the second reactor effluent 110, the third reactor feed 111, the third reactor effluent 112, the fourth reactor feed 113, or combinations thereof. In addition, the oxygenate and/or nitrogenate stream can be added to fourth reactor effluent 114, hydrogen stream 115, dry hydrogen recycle 116, reformate 117, recycle stream 119, or combinations thereof.

Furthermore, the oxygenate and/or nitrogenate stream can be added to any combination of the aforementioned streams, directly to any of reactors 10, 20, 30, or 40, directly to furnaces 11, 21, 31, 41, or combinations thereof. Likewise, the oxygenate and/or nitrogenate stream can be added directly to any other process equipment or component of catalytic reactor system 100 such as a pump, value, port, tee, manifold, etc. Finally, it is possible to add the oxygenate and/or nitrogenate stream to any process equipment or component upstream of catalytic reactor system 100 such as a tank, pump, value, port, tee, manifold, and the like that supplies the feed 101 to the catalytic reactor system.

The addition of oxygenates and/or nitrogenates to a reforming process is described in detail in U.S. Pat. No. 7,932,425, which is incorporated herein by reference in its entirety. All manner of addition described therein can be used in the aromatization processes as described herein.

In embodiments, the effluent from the catalytic reforming process can comprise at least about 40 wt % of the primary aromatic hydrocarbons based on the total weight of the effluent. In other embodiments, the effluent from the catalytic reforming process can comprise from about 40 wt % to about 80 wt % of the primary aromatic hydrocarbons based on the total weight of the effluent. In some embodiments, the catalytic reforming process can achieve from about 60% to about 100% conversion on a molar basis with at least about 80% selectivity on a molar basis. In a preferred embodiment, the catalytic reforming process can achieve at least about 80% conversion, 81% conversion, 82% conversion, 83% conversion, 84% conversion, or 85% conversion on a molar basis and at least about 80% selectivity on a molar basis. In some embodiments, the primary aromatic hydrocarbons can comprise toluene, benzene, styrene, and the like.

Referring again to FIG. 1, hydrogen stream 115 can, in some embodiments, be recycled and added into purified feed 103. Specifically, hydrogen stream 115 can pass through a dryer 60 to produce a dried hydrogen recycle stream 116, which can be added to purified feed 103 to form the reactor feed stream 106. Hydrogen is often used as a diluent heat source as it serves to not only lower the partial pressure of the cyclic hydrocarbon, but also suppresses the formation of hydrogen deficient, carbonaceous deposits, commonly referred to as "coke," on the catalytic composite. However, hydrogen has a relatively low heat capacity compared to heavy aromatic hydrocarbons and further can inhibit forward progress of the aromatization reaction. Specifically, because hydrogen is a product of the desired aromatization reaction, an excess concentration of hydrogen in the reaction zone 120 can inhibit forward progress of the reaction by causing the aromatization reaction to reach equilibrium at lower conversion rates than if a hydrogen diluent were not used. In some embodiments, when hydrogen stream 115 is recycled and added into purified feed 103, the heat capacity of reactor feed stream 106 is higher than the heat capacity of feed 101. In other words, in some embodiments when hydrogen stream 115 is recycled and added into purified feed 103, higher heat capacity materials, such as those present in recycle stream 119, are also added, such that the heat capacity of the reactor feed stream 106, which comprises a combination of the components of the feed 101, hydrogen stream 115, and recycle stream 119, is higher than the heat capacity of the feed 101.

Reformate 117 is fed to purification-extraction process 70, which separates recycle stream 119 comprising heavy aromatic hydrocarbons from raffinate 125 and from primary aromatic hydrocarbon product 118. In some embodiments, purification-extraction process 70 further comprises a sulfur converter-absorber. In some embodiments, recycle stream 119 is passed through a sulfur converter-absorber and then is added to fractionator 122. In some embodiments, recycle stream 119 does not pass through a recycle line compressor. In other embodiments, recycle stream 119 does pass through a recycle line compressor. For the sake of simplicity, FIG. 1 does not illustrate the by-product streams that can be removed from catalytic reactor system 100 at various points throughout the system. However, persons of ordinary skill in the art are aware of the composition and location of such by-product streams.

In some embodiments, raffinate 125 can be recycled into feed 101 and primary aromatic hydrocarbons product stream 118 is sold or otherwise used as desired. In some embodiments, raffinate 125 can be recycled into feed 101 through a second return line. In some embodiments, raffinate 125 can be recycled into fractionator 122. In some embodiments, raffinate 125 can be recycled into fractionator 122 through a second return line. In some embodiments, primary aromatic hydrocarbons product stream 118 can comprise benzene, toluene, or any combinations thereof. In some embodiments, primary aromatic hydrocarbons product stream 118 comprises benzene. In some embodiments, primary aromatic hydrocarbons product stream 118 comprises benzene and toluene. In some embodiments, primary aromatic hydrocarbons product stream 118 comprises toluene. In some embodiments, primary aromatic hydrocarbons product stream 118 comprises benzene and recycle stream 119 comprises toluene and xylenes. In some embodiments, primary aromatic hydrocarbons product stream 118 comprises benzene and recycle stream 119 comprises toluene. In some embodiments, primary aromatic hydrocarbons product stream 118 comprises toluene and recycle stream 119 comprises xylenes.

In some embodiments, recycle stream 119 can be produced as a product. For example, in some embodiments, a portion of recycle stream 119 can be sent to downstream processing, while a portion of recycle stream 119 is recycled to form part of the combined stream 102. In some embodiments, the aromatic hydrocarbons in recycle stream 119 are added to feedstock 101 to form combined stream 102 at a rate of from about 1 mole to about 5 mole per mole of aliphatic hydrocarbons in feedstock 101, for example, about 1 mole, about 1.5 moles, about 2 moles, about 2.5 moles, about 3 moles, about 3.5 moles, about 4 moles, about 4.5 moles, or about 5 moles of aromatic hydrocarbons in recycle stream 119 can be added to feedstock 101 to form combined stream 102 per 1 mole of aromatic hydrocarbons in the feedstock 101.

In some embodiments, primary hydrocarbon product 118 can be further separated into a $C_6$ aromatic hydrocarbon product and a heavy, for example $C_7$-$C_8$, aromatic hydrocarbon product. For example, in some embodiments, primary hydrocarbon product 118 can be further separated into a benzene product and a toluene product. In some embodiments, the primary hydrocarbon product 118 can be further separated into a benzene product and a xylene product. In some embodiments, primary hydrocarbon product 118 can be further separated into a benzene product and a heavy aromatic hydrocarbon product comprising toluene and xylene. In some embodiments, the heavy aromatic hydrocarbon product can be added to recycle stream 119.

In some embodiments, the temperature of feed stream 106 (which can be the first temperature) is within from about 10° F. (5.5° C.) to about 90° F. (50° C.) of the temperature of the first reactor feed 107 (which can be the second temperature), for example within about 10° F. (5.5° C.), about 20° F. (11° C.), about 30° F. (16° C.), about 40° F. (22° C.), about 50° F. (28° C.), about 60° F. (33° C.), about 70° F. (39° C.), about 80° F. (44° C.), or about 90° F. (50° C.). While not intending to be bound by theory, it is believed that, when feed stream 106 has a higher heat capacity than feedstock 101 as described above, the temperature drop across each of reactors 10, 20, 30, and 40 will be smaller than if the heat capacity of feed stream 106 were the same as or lower than feedstock 101. In other words, and while not theory bound, it is believed that, when feed stream 106 has a higher heat capacity than feedstock 101 as described above, the difference in temperature between each of first reactor feed stream 106 and first reactor effluent 108, second reactor feed stream 109 and second reactor effluent 110, third reactor feed stream 111 and third reactor effluent 112, and fourth reactor feed stream 113 and fourth reactor effluent 114 will be smaller than if the heat capacity of feed stream 106 were the same as or lower than feedstock 101. Similarly and while not intending to be bound by theory, it is believed that when feed stream 106 has a higher heat capacity than feedstock 101 as described above, each furnace 11, 21, 31, and 41 can heat each of reactor feed streams 107, 109, 111, and 113 to lower temperatures than if the heat capacity of feed stream 106 were the same as or lower than feedstock 101, and yet still achieve the same conversion rates. It is also believed that, if each furnace, 11, 21, 31, and 41 can heat each of the reactor feed streams, 107, 109, 111, and 113, to lower temperatures, then the required heat duty provided by any one of the furnaces and/or the total heat duty provided by all of the furnaces will decrease.

In an aspect, the process for producing aromatic hydrocarbons can further include the step of returning the heavy aromatic hydrocarbon product to recycle stream 119 (also, the diluent input line) for addition to reactor feedstock 101, wherein the first temperature (for example, of feed stream 106) is within from about 10° F. (5.5° C.) to about 90° F. (50° C.) of the second temperature (for example of reactor feed stream 107), depending upon the amount (weight percent) of heavy aromatic diluent added. Without returning some of the heavy aromatic hydrocarbon product to the diluent input line, the difference between the first temperature and the second temperature can be from about 100° F. (55° C.) to about 120° F. (66° C.). With the addition of some heavy aromatic hydrocarbon product, the temperature difference between the first and the second temperatures is roughly the temperature without the addition (for example, 120° F. (66° C.)) times (1−weight fraction) of the heavy aromatic diluent, with all other variables (e.g. feedstock, conversion, catalyst, etc.) being constant. Therefore, when 40 wt % diluent is added, the 120° F. (66° C.) temperature difference is lowered to about 72° F. (40° C.). As 100% diluent is approached, the reaction becomes isothermal. In this aspect, the first temperature plus the second temperature divided by two (average of the first and second temperatures) can be lower than when the high heat capacity heavy aromatic hydrocarbon product is not recycled, and still provide the same level of conversion.

While not intending to be bound by theory, it is believed that when feed stream 106 has a higher heat capacity than feedstock 101 as a result of returning the higher heat capacity heavy aromatic hydrocarbon product to recycle stream (or diluent input line) 119, each furnace 11, 21, 31, and 41 can heat each of reactor feed streams 107, 109, 11, and 113 to lower temperatures than if the heat capacity of feed stream 106 were the same as or lower than the heat capacity of feedstock 101, and yet still achieve the same conversion rates. In an aspect, for example, the step of returning the heavy aromatic hydrocarbon product to the diluent input line for addition to the reactor feedstock can be carried out, wherein the difference between the first temperature (of feed stream 106) and the second temperature (of reactor feed stream 107) can be from about 10° F. (5.5° C.) to about 90° F. (50° C.) of the temperature of first reactor feed 107, for example within about 10° F. (5.5° C.), about 20° F. (11° C.), about 30° F. (16° C.), about 40° F. (22° C.), about 50° F. (28° C.), about 60° F. (33° C.), about 70° F. (39° C.), about 80° F. (44° C.), or about 90° F. (50° C.). Under these conditions of returning the heavy aromatic hydrocarbon product to the diluent input line for addition to the reactor feedstock, the first temperature plus the second temperature divided by two can be lower than when the high heat capacity heavy aromatic hydrocarbon product is not recycled, and still provide the same level of conversion. In an embodiment, the heat duty provided by each furnace to heat each of the reactor feed streams can be reduced by about 5%, 10%, 15%, 20%, 25%, 30%, 35%, 40%, 50%, 55%, or 60% when feed stream 106 has a higher heat capacity compared to the heat capacity of feedstock 101. In an embodiment, the total heat duty provided by all of the furnaces can be reduced by about 5%, 10%, 15%, 20%, 25%, 30%, 35%, 40%, 50%, 55%, or 60% when feed stream 106 has a higher heat capacity compared to the heat capacity of feedstock 101.

In some embodiments, primary aromatic hydrocarbon product 118 and feed stream 106 can be analyzed according to methods known in the art to determine their chemical composition, and the composition of feed stream 106 is adjusted to maintain or achieve a desired heptane to toluene molar ratio. For example, the composition of feed stream 106 is adjusted to maintain a heptane to toluene molar ratio of from about 1:10 to about 20:1. In an embodiment, the heptane to toluene molar ratio can be about 1:5, 1:3, 2:5, 1:2, 3:5, 3:4, 4:5, or 1:1. In another embodiment, the heptane to toluene molar ratio can be about 1:1, 2:1, 3:1, 4:1, 5:1, 6:1, 7:1, 8:1, 9:1, or 10:1. In another embodiment, the heptane to toluene molar ratio can be about 10:1, 11:1, 12:1, 13:1, 14:1, 15:1, 16:1, 17:1, 18:1, 19:1, or 20:1. This heptane to toluene molar ratio can be maintained by adjusting the composition of feedstock 101, or by adjusting the composition and relative amounts of components which are recycled and added to purified stream 103, such as recycle stream 119, oxygenate and/or nitrogenate stream 105, raffinate 125, and hydrogen stream 115. For example, when feedstock 101 comprises heptane and toluene is not a desired component of primary aromatic hydrocarbon product 118, maintaining a relatively low molar ratio of heptane to toluene in feed stream 106 will reduce the reaction of heptane to toluene, and allow the system to instead produce more of the desired primary aromatic hydrocarbon product 118, such as benzene. In some embodiments, this heptane to toluene molar ratio can be maintained by adjusting the flow rate of recycle stream 119. While not intending to be bound by theory, in these embodiments, the toluene present in recycle stream 119 can also act as a diluent heat source in reactors 10, 20, 30, and 40.

Hydrogen separation processes 50 and purification-extraction processes 70 are well known in the art and are described in numerous patents, for example, U.S. Pat. No. 5,401,386 to Morrison et al. entitled "Reforming Process for Producing High-Purity Benzene," U.S. Pat. No. 5,877,367 to Witte entitled "Dehydrocyclization Process with Downstream Dimethylbenzene Removal", and U.S. Pat. No. 6,004,452 to Ash et al. entitled "Process for Converting Hydrocarbon Feed to High Purity Benzene and High Purity Paraxylene," each of which is incorporated herein by reference in its entirety. Generally, the extraction is either a liquid/liquid extraction (for example, using sulfolane as the solvent) or an extractive distillation. According to one embodiment, extractive distillation involves extractive distillation with N-substituted morpholines as the extractive distillation solvent. According to another embodiment, the extraction unit comprises an extractive distillation unit using a N-formylmorpholine solvent. Such a unit generally comprises an extractive distillation column and a stripper column. The extractive distillation column contacts the light fraction with the N-formylmorpholine solvent, suppressing the boiling point of the aromatic hydrocarbons and allowing the non-aromatic hydrocarbons to be taken overhead. The stripper column separates the remaining aromatic hydrocarbons from the N-formylmorpholine solvent using simple distillation. The non-aromatic hydrocarbon raffinate recovered from the extraction process can be recycled and added to the feed, which can increase overall yield of the process.

In some embodiments, catalytic reactor system 100 can be operated during catalyst startup at a gas flow rate comprising a GHSV of between about 400 and about 2000 hr$^{-1}$, for example 400 hr$^{-1}$, about 500 hr$^{-1}$, about 600 hr$^{-1}$, about 700 hr$^{-1}$, about 800 hr$^{-1}$, about 900 hr$^{-1}$, about 1000 hr$^{-1}$, about 1100 hr$^{-1}$, about 1200 hr$^{-1}$, about 1300 hr$^{-1}$, about 1400 hr$^{-1}$, about 1500 hr$^{-1}$, about 1600 hr$^{-1}$, about 1700 hr$^{-1}$, about 1800 hr$^{-1}$, about 1900 hr$^{-1}$, or about 2000 hr$^{-1}$. In some embodiments, catalytic reactor system 100 can be operated during catalyst startup at a heat-up rate of between 5° F./hr (3° C./hr) and 50° F./hr (28° C./hr) during catalyst reduction above about 500° F. (260° C.), for example about 5° F./hr (3° C./hr), about 10° F./hr (5.5° C./hr), about 15° F./hr (8° C./hr), about 20° F./hr (11° C./hr), about 25° F./hr (14° C./hr), about 30° F./hr (16° C./hr), about 35° F./hr (19° C./hr), about 40° F./hr (22° C./hr), about 45° F./hr (25° C./hr), or about 50° F./hr (28° C./hr).

For example, in some embodiments wherein the catalyst comprises a halide zeolite catalyst, catalytic reactor system 100 can be operated during catalyst startup at a gas flow rate comprising a GHSV of between about 400 and about 2000 hr$^{-1}$, for example 400 hr$^{-1}$, about 500 hr$^{-1}$, about 600 hr$^{-1}$, about 700 hr$^{-1}$, about 800 hr$^{-1}$, about 900 hr$^{-1}$, about 1000 hr$^{-1}$, about 1100 hr$^{-1}$, about 1200 hr$^{-1}$, about 1300 hr$^{-1}$, about 1400 hr$^{-1}$, about 1500 hr$^{-1}$, about 1600 hr$^{-1}$, about 1700 hr$^{-1}$, about 1800 hr$^{-1}$, about 1900 hr$^{-1}$, or about 2000 hr$^{-1}$ and at a heat-up rate of between 5° F./hr (3° C./hr) and 50° F./hr (28° C./hr) during catalyst reduction above about 500° F. (260° C.), for example about 5° F./hr (3° C./hr), about 10° F./hr (5.5° C./hr), about 15° F./hr (8° C./hr), about 20° F./hr (11° C./hr), about 25° F./hr (14° C./hr), about 30° F./hr (16° C./hr), about 35° F./hr (19° C./hr), about 40° F./hr (22° C./hr), about 45° F./hr (25° C./hr), or about 50° F./hr (28° C./hr).

In some embodiments wherein the catalyst comprises a fluorided zeolite platinum catalyst, catalytic reactor system 100 can be operated during catalyst startup at a gas flow rate comprising a GHSV of between about 600 and about 1500 hr$^{-1}$, for example about 600 hr$^{-1}$, about 700 hr$^{-1}$, about 800 hr$^{-1}$, about 900 hr$^{-1}$, about 1000 hr$^{-1}$, about 1100 hr$^{-1}$, about 1200 hr$^{-1}$, about 1300 hr$^{-1}$, about 1400 hr$^{-1}$, or about 1500 hr$^{-1}$, and at a heat-up rate of between 10° F./hr (5.5° C./hr) and 30° F./hr (16° C./hr) during catalyst reduction above about 500° F. (260° C.), for example about 10° F./hr (5.5° C./hr), about 15° F./hr (8° C./hr), about 20° F./hr (11° C./hr), about 25° F./hr (14° C./hr), or about 30° F./hr (16° C./hr).

In some embodiments wherein the catalyst comprises a fluoride-chlorided zeolite platinum catalyst, catalytic reactor system 100 can be operated during catalyst startup at a gas flow rate comprising a GHSV of between about 600 and about 1500 hr$^{-1}$, for example about 600 hr$^{-1}$, about 700 hr$^{-1}$, about 800 hr$^{-1}$, about 900 hr$^{-1}$, about 1000 hr$^{-1}$, about 1100 hr$^{-1}$, about 1200 hr$^{-1}$, about 1300 hr$^{-1}$, about 1400 hr$^{-1}$, or about 1500 hr$^{-1}$ and at a heat-up rate of between 10° F./hr (5.5° C./hr) and 25° F./hr (14° C./hr) during catalyst reduction above about 500° F. (260° C.), for example about 10° F./hr (5.5° C./hr), about 15° F./hr (8° C./hr), about 20° F./hr (11° C./hr), or about 25° F./hr (14° C./hr).

The Catalyst

The aromatization catalyst can comprise an inorganic support, a Group 8-10 metal such as platinum, and one or more halides such as fluorine, chlorine, iodine, bromine, or combinations thereof, such as the hiz-cat catalysts described in U.S. Pat. No. 6,190,539 to Holtermann et al., which is incorporated herein by reference. In some embodiments, the catalyst can comprise Group 8-10 metals on an inorganic support such as platinum on alumina, Pt/Sn on alumina and Pt/Re on alumina. In other embodiments, the catalyst can comprise noble Group 8 metals such as Pt, Pt/Sn and Pt/Re on zeolitic supports which can comprise a binder and zeolites such as L-zeolites, ZSM-5, silicalite and beta; and noble Group 8 metals on alkali- and alkaline-earth exchanged L-zeolites. The catalyst can comprise a large-pore zeolite as the inorganic support that is charged with at least one Group 8-10 metal. In embodiments, the Group 8-10 metal can comprise platinum, which can be more selective for dehydrocyclization and which can be more stable under reforming reaction conditions than other Group 8-10 metals. In other embodiments, the catalyst can comprise a Group 7 metal such as rhenium, or a Group 14 metal or metalloid such as tin.

In one embodiment, the catalyst can comprise a non-acidic catalyst which can comprise a non-acidic zeolite support as the inorganic support, a Group 8-10 metal or other suitable metals, and one or more halides. Suitable halides include chloride, fluoride, bromide, iodide, or combinations thereof. Suitable Group 8-10 metals include iron, cobalt, nickel, ruthenium, rhodium, palladium, osmium, iridium, platinum, or combinations thereof.

Inorganic supports for aromatization catalysts (also termed reforming catalysts) can generally include any inorganic oxide. These inorganic supports include bound large pore aluminosilicates (zeolites), amorphous inorganic oxides, and mixtures thereof. Large pore aluminosilicates include, but are not limited to, L-zeolite, Y-zeolite, mordenite, omega zeolite, beta zeolite, and the like. Amorphous inorganic oxides include, but are not limited to, aluminum oxide, silicon oxide, and titania. Suitable bonding agents for the inorganic supports include, but are not limited to, silica, alumina, clays, titania, magnesium oxide, and combinations thereof.

The inorganic support can be an aluminosilicate, for example a zeolite. In embodiments, the aromatization catalyst can comprise a zeolitic catalyst. Zeolite materials, both natural and synthetic, can have appropriate catalytic properties for many hydrocarbon processes, including aromatization. Thus, zeolites can include the group of natural or synthetic hydrated aluminosilicate minerals that typically contain alkali and alkaline metals. Zeolites are characterized by a framework structure that encloses interconnected cavities occupied by ion-exchangeable large metal cations such as potassium and water molecules permitting reversible dehydration. The actual formula of the zeolite can vary without changing the crystalline structure. In an embodiment, the mole ratio of silicon to aluminum (Si/Al) in the zeolite can vary from about 1.0 to about 3.5.

The inorganic support can further be any of a clay mineral, silica, alumina, silica-alumina, aluminum phosphate, a heteropolytungstate, titania, zirconia, magnesia, boria, zinc oxide, mixed oxides thereof, a silica-bound zeolite, or mixtures thereof.

In embodiments, the aromatization catalyst can comprise a large pore zeolite. The term "large-pore zeolite" can be defined as a zeolite having an effective pore diameter of from about 6 Angstroms (Å) to about 15 Å; alternatively, from about 7 Å to about 9 Å. Examples of large pore crystalline zeolites are type L-zeolite, zeolite X, zeolite Y, omega zeolite, beta zeolite, ZSM-4, ZSM-5, ZSM-10, ZSM-12, ZSM-20, REY, USY, RE-USY, LZ-210, LZ-210-A, LZ-210-M, LZ-210-T, SSZ-24, SSZ-26, SSZ-31, SSZ-33, SSZ-35, SSZ-37, SSZ-41, SSZ-42, SSZ-44, ZZA-26, MCM-58, mordenite, mazzite, faujasite, and combinations thereof. In one embodiment, the large pore zeolite can comprise an isotypic framework structure. In one embodiment, the aromatization catalyst can comprise L-zeolite.

L-Zeolite, its x-ray diffraction pattern, its properties, and methods for its preparation are described in detail in, U.S. Pat. No. 3,216,789, the content of which is hereby incorporated by reference. Zeolite X is described in U.S. Pat. No. 2,882,244. Mazzite is described in U.S. Pat. Nos. 4,503,023 and 4,021,447. Mordenite is described in U.S. Pat. No. 4,503,023. Zeolite Y is described in U.S. Pat. No. 3,130,007. U.S. Pat. Nos. 3,216,789; 2,882,244; 4,503,023; 4,021,447; and 3,130,007, are hereby incorporated herein by reference to show zeolites useful for aromatization processes.

In embodiments, the aromatization catalyst can comprise a large pore L-zeolite. L-type zeolite catalysts are a subgroup of zeolitic catalysts. Typical L-type zeolites contain mole ratios of oxides in accordance with the following formula:

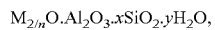

$$M_{2/n}O.Al_2O_3.xSiO_2.yH_2O,$$

wherein "M" designates at least one exchangeable cation such as barium, calcium, cerium, lithium, magnesium, potassium, sodium, strontium, and zinc as well as nonmetallic cations like hydronium and ammonium ions which can be replaced by other exchangeable cations without causing a substantial alteration of the basic crystal structure of the L-type zeolite. The "n" in the formula represents the valence of "M", "x" can be 2 or greater; and "y" is the number of water molecules contained in the channels or interconnected voids with the zeolite.

Bound potassium L-type zeolites, or KL zeolites, have been found to be particularly desirable. The term KL zeolite as used herein refers to L-type zeolites in which the principal cation M incorporated in the zeolite can comprise potassium. A KL zeolite can be cation-exchanged or impregnated with another metal and one or more halides to produce a platinum-impregnated, halided zeolite or a KL supported Pt-halide zeolite catalyst. In one embodiment, the zeolite can comprise type L zeolite. In embodiments, the aromatization catalyst can comprise a potassium L-type zeolite, hereafter referred to as KL-zeolite, which refers to L-type zeolites wherein the principal exchangeable cation M incorporated in the zeolite is potassium.

One or more Group 8-10 metals or other suitable metals such as rhenium can be added to the catalyst support to form a metallized catalyst support. The metal can be added to the catalyst support by employing a variety of known and conventional techniques, e.g., ion-exchange, incipient wetness, pore fill, impregnation, vapor deposition etc. In embodiments, the platinum and optionally one or more halides can be added to the zeolite support by any suitable method, for example via impregnation with a solution of a platinum-containing compound and one or more halide-containing compounds. In one embodiment, the metal can be added to the catalyst support by impregnation with a metal-containing solution. The metal in the metal containing solution can comprise at least one metal from Group 8-10; alternatively, ruthenium, osmium, rhodium, iridium, palladium or platinum, or combinations thereof. In one embodiment, the metal can comprise platinum that can be added to the catalyst support via contact with a metal-containing solution containing at least one platinum-containing compound. Examples of suitable platinum-containing compounds for contact with the catalyst support include, without limitation, platinum compounds that form positively charged platinum complex ions in solution such as, for example, platinum salts such as chlorides and nitrates; platinum complexes with amines; or combinations thereof. For example, the platinum-containing compound can be any decomposable platinum-containing compound including, but not limited to, ammonium tetrachloroplatinate, chloroplatinic acid, diammineplatinum (II) nitrite, bis(ethylenediamine)-platinum (II) chloride, platinum (II) acetylacetonate, dichlorodiammine platinum, platinum (II) chloride, tetraammineplatinum (II) hydroxide, tetraammineplatinum chloride, and tetraammineplatinum (II) nitrate. In one embodiment, the platinum source can comprise tetraamine platinum chloride (TAPC). The amount of platinum in the metallized catalyst support can range from about 0.1 to about 5 wt %; for example, from about 0.1 to about 3 wt %; for example, from about 0.3 to about 1.8 wt %.

In an aspect, the catalyst can comprise a large pore zeolite support with a platinum-containing compound and at least one halide. One or more halides can be added to the catalyst support by contact with a halide-containing compound to form a halided catalyst support. The halides can be added into the catalyst support separately; alternatively, the halides can be added to the catalyst support at the same time. Such halides can be incorporated during addition of a metal, alternatively, the halides can be incorporated in a separate step that can be pre- or post-addition of the metal, to form a halided, metallized catalyst support. Examples of suitable halides include, without limitation, fluoride, chloride, bromide, iodide, or combinations thereof. Such halides can be introduced, for example, as the ammonium halide compound.

In one embodiment, the catalyst can comprise a large pore zeolite support with a platinum-containing compound and at least one ammonium halide compound. The ammonium halide compound can comprise one or more compounds represented by the formula [NR$_4$]X, where X can comprise a halide and where R represents a hydrogen or a substituted or unsubstituted carbon chain molecule having about 1 to about 20 carbons wherein each R can be the same or different. In one embodiment, R can comprise methyl, ethyl, propyl, butyl, or combinations thereof. Examples of a suitable organic ammonium compound represented by the formula [NR$_4$]X can include ammonium chloride, ammonium fluoride, and tetraalkylammonium halides such as tetramethylammonium chloride (TMAC), tetramethylammonium fluoride (TMAF), tetraethylammonium chloride, tetraethylammonium fluoride, tetrapropylammonium chloride, tetrapropylammonium fluoride, tetrabutylammonium chloride, tetrabutylammonium fluoride, methyltriethylammonium chloride, methyltriethylammonium fluoride, or combinations thereof.

In an aspect, the ammonium halide compound can comprise at least one acid halide and at least one ammonium hydroxide represented by the formula [NR'$_4$]OH, where R' can comprise hydrogen or a substituted or unsubstituted carbon chain molecule having about 1 to about 20 carbon atoms wherein each R' can be the same or different. In one embodiment, R' can comprise methyl, ethyl, propyl, butyl, or combinations thereof. Examples of a suitable ammonium hydroxide represented by the formula [NR'$_4$]OH can include ammonium hydroxide, tetraalkylammonium hydroxides such as tetramethylammonium hydroxide, tetraethylammonium hydroxide, tetrapropylammonium hydroxide, tetrabutylammonium hydroxide, and combinations thereof. Examples of suitable acid halides can include HCl, HF, HBr, HI, or combinations thereof.

In another aspect, the ammonium halide compound can comprise (a) a compound represented by the formula [NR$_4$]X, where X can comprise a halide and where R represents a hydrogen or a substituted or unsubstituted carbon chain molecule having about 1 to about 20 carbons wherein each R can be the same or different, and (b) at least one acid halide and at least one ammonium hydroxide represented by the formula [NR'$_4$]OH, where R' can comprise hydrogen or a substituted or unsubstituted carbon chain molecule having about 1 to about 20 carbon atoms wherein each R' can be the same or different.

The halide-containing compound can further comprise an ammonium halide such as ammonium chloride, ammonium fluoride, or both in various combinations with the ammonium halide compounds described previously. More specifically, ammonium chloride, ammonium fluoride, or both can be used with (a) as described previously, a compound represented by the formula [NR$_4$]X, where X can comprise a halide and where R represents a hydrogen or a substituted or unsubstituted carbon chain molecule having about 1 to about 20 carbons wherein each R can be the same or different and/or (b) as described previously, at least one acid halide and at least one organic ammonium hydroxide represented by the formula [NR'$_4$]OH, where R' can comprise a substituted or unsubstituted carbon chain molecule having about 1 to about 20 carbon atoms wherein each R' can be the same or different. For example, a first fluoride- or chloride-containing compound can be introduced as a tetraalkylammonium halide with a second fluoride- or chloride-containing compound introduced as an ammonium halide. In one embodiment, tetraalkylammonium chloride can be used with ammonium fluoride. In another embodiment, ammonium chloride can be used with ammonium fluoride.

In one aspect, the aromatization catalyst can comprise a metallized, halided support, and the amount of halide in the catalyst ranges from about 0.05 wt % to about 5.0 wt %. In one embodiment, the halided catalyst support can comprise chloride present in an amount of from about 0.1 wt % to about 5 wt %; for example, from about 0.1 wt % to about 3 wt %; for example, from about 0.3 wt % to about 1.8 wt %. In one embodiment, the halided catalyst support can comprise fluoride present in an amount of from about 0.1 wt % to about 5 wt %; for example, from about 0.1 wt % to about 3 wt %; for example, from about 0.3 wt % to about 1.8 wt %. In one embodiment, the halided catalyst support can comprise both chloride and fluoride, which can be present in a Cl:F ratio of from about 1:10 to about 10:1; for example, from about 1:5 to about 5:1; for example, from about 1:2 to about 2:1.

Examples of suitable aromatization catalysts are also disclosed in U.S. Pat. No. 7,153,801 to Wu entitled "Aromatization Catalyst and Methods of Making and Using Same," and U.S. Pat. No. 6,812,180 to Fukunaga entitled "Method for Preparing Catalyst," each of which is incorporated herein by reference in their entirety.

The processes as described can be carried out with any art recognized selective catalysts. In one embodiment, the catalyst for use in the described process can comprise a low-acidity silica-bound potassium L-type zeolite support, platinum, chloride, and fluoride. In this embodiment, the aromatization catalyst selectively converts near-linear $C_6$ hydrocarbons (i.e., $C_6$ hydrocarbons with no more than one branch), but may not readily convert $C_6$ hydrocarbons having more than one branch, e.g., dimethylpentane. This selective catalyst readily converted near-linear $C_6$ hydrocarbons to aromatic hydrocarbons at greater than about 75 mol. % aromatics selectivity; for example, greater than about 80 mol. % aromatics selectivity; for example, greater than about 83 mol. % aromatics selectivity.

Catalysts for use in the process as described generally see a decline in catalytic activity that occurs as the catalyst is used under commercial reaction conditions. A catalyst is generally considered spent when it has reached an unacceptable level in one or more of activity, conversion, selectivity, yield or other operating parameter. Regenerable catalysts are appropriate for use in the processes as described, and the catalysts can be subjected to any regeneration chemistry as recognized by one of ordinary skill in the art. For example, transition metal catalysts are often regenerated by contacting the spent catalyst with a halogen-containing stream, e.g., chlorine or fluorine, and then decoking the catalyst in an oxygen stream.

The aromatization reactions can occur under process conditions that thermodynamically favor the dehydrocyclization (aromatization) reaction and limit the undesirable hydrocracking reactions. Operating ranges for a typical catalytic aromatization process, such as an aromatization process as disclosed herein, can include reactor inlet temperatures between about 370° C. and about 570° C., for example between about 430° C. and about 550° C.; a system pressure between about 0 pounds per square inch gauge (psig) and about 580 psig (4,000 kPa), for example from about 0 psig to about 365 psig (2516 kPa); a hydrogen rate sufficient to yield a hydrogen to hydrocarbon mole ratio for the feed to the reforming reactor zone between about 0.1 and about 20, for example from about 3 to about 10, for example from about 1.5 to about 6; and, a liquid hourly space velocity for the hydrocarbon feed over the aromatization catalyst of between about 0.1 hr$^{-1}$ and about 10 hr$^{-1}$.

Examples of catalysts and reactor systems suitable for use with the methods described herein are the AROMAX® Process and catalyst technologies available from the Chevron Phillips Chemical Company of The Woodlands, Tex., USA. A specific example of a suitable commercially available aromatization catalyst is the AROMAX® II Catalyst available from Chevron Phillips Chemical Company LP of The Woodlands, Tex., USA.

EMBODIMENTS

Embodiment 1

A process for producing aromatic hydrocarbons comprising:

adding a diluent comprising a heavy aromatic hydrocarbon to a reactor feedstock comprising aliphatic hydrocarbons or light naphtha to form a reactant feed stream at a first temperature;

heating the reactant feed stream in a furnace to a second temperature;

contacting the heated reactant feed stream with a catalyst comprising an inorganic support, a Group 8-10 metal, and halide under conditions for aromatizing at least a portion of the aliphatic hydrocarbons, thereby forming a reactor effluent stream at a third temperature, the reactor effluent stream comprising a primary aromatic hydrocarbon product and a heavy aromatic hydrocarbon product;

separating the reactor effluent stream into the primary aromatic hydrocarbon product, the heavy aromatic hydrocarbon product, hydrogen, and a raffinate; and forming the diluent from the heavy aromatic hydrocarbon product;

wherein forming the diluent comprises adding the heavy aromatic hydrocarbon having at least one carbon atom more than the primary aromatic hydrocarbon product.

Embodiment 2

A catalytic hydrocarbon reforming system comprising:

a fractionator having an inlet to receive an initial feedstock comprising naphtha and an outlet to discharge a reactor feedstock comprising aliphatic hydrocarbons or light naphtha;

a diluent input line for adding a diluent comprising a heavy aromatic hydrocarbon to the reactor feedstock to form a reactant feed stream having a first temperature;

at least one furnace capable of heating the reactant feed stream to a second temperature;

at least one reactor charged with a catalyst comprising an inorganic support, a Group 8-10 metal, and at least one halide, the reactor having an inlet to receive the reactant feed stream and an outlet to discharge a reactor effluent stream at a third temperature, the reactor effluent stream comprising a primary aromatic hydrocarbon product and a heavy aromatic hydrocarbon product;

a separation system that receives the reactor effluent stream and separately discharges the primary aromatic hydrocarbon product, the heavy aromatic hydrocarbon product, hydrogen, and a raffinate;

a first return line extending from the separation system to the diluent input line for providing the diluent, the diluent comprising at least a portion of the heavy aromatic hydrocarbon product;

separating the reactor effluent stream into the primary aromatic hydrocarbon product, the heavy aromatic hydrocarbon product, hydrogen, and a raffinate;

forming the diluent from the heavy aromatic hydrocarbon product; and wherein forming the diluent comprises adding the heavy aromatic hydrocarbon having at least one carbon atom more than the primary aromatic hydrocarbon product.

Embodiment 3

A process for producing aromatic hydrocarbons or a catalytic hydrocarbon reforming system according to any one of embodiments 1 or 2, wherein the reactor feedstock and reactant stream comprise $C_6$ to $C_8$ aliphatic hydrocarbons.

Embodiment 4

A process for producing aromatic hydrocarbons or a catalytic hydrocarbon reforming system according to any one of embodiments 1 or 2, wherein the reactor feedstock and reactant stream comprise light naphtha.

Embodiment 5

A process for producing aromatic hydrocarbons or a catalytic hydrocarbon reforming system according to any one of embodiments 1-4, wherein the reactant feed stream further comprises a stabilizer selected from one or more $C_7$-$C_{10}$ paraffins.

Embodiment 6

A process for producing aromatic hydrocarbons or a catalytic hydrocarbon reforming system according to any one of embodiments 1-5, wherein the aromatic hydrocarbons in the diluent are added in an amount of from about 1 mole to about 5 mole per mole of aliphatic hydrocarbons in the reactor feedstock.

Embodiment 7

A process for producing aromatic hydrocarbons or a catalytic hydrocarbon reforming system according to any one of embodiments 1-6, wherein the diluent comprises toluene.

Embodiment 8

A process for producing aromatic hydrocarbons or a catalytic hydrocarbon reforming system according to any one of embodiments 1-5, wherein the diluent comprises toluene and xylenes.

Embodiment 9

A process for producing aromatic hydrocarbons or a catalytic hydrocarbon reforming system according to any one of embodiments 1-8, wherein the diluent further comprises $C_{9+}$ aromatic hydrocarbon compounds.

Embodiment 10

A process for producing aromatic hydrocarbons or a catalytic hydrocarbon reforming system according to any one of embodiments 1-9, wherein the diluent further comprises hydrogen.

Embodiment 11

A process for producing aromatic hydrocarbons or a catalytic hydrocarbon reforming system according to any one of embodiments 1-10, wherein the primary aromatic hydrocarbon product comprises benzene.

Embodiment 12

A process for producing aromatic hydrocarbons or a catalytic hydrocarbon reforming system according to any one of embodiments 1-10, wherein the primary aromatic hydrocarbon product comprises benzene and toluene.

Embodiment 13

A process for producing aromatic hydrocarbons or a catalytic hydrocarbon reforming system according to any one of embodiments 1-10, wherein the heavy aromatic hydrocarbon product comprises toluene and xylenes.

Embodiment 14

A process for producing aromatic hydrocarbons or a catalytic hydrocarbon reforming system according to any one of embodiments 1-10, wherein the heavy aromatic hydrocarbon product comprises toluene, xylenes, and $C_{9+}$ aromatic compounds.

Embodiment 15

A process for producing aromatic hydrocarbons or a catalytic hydrocarbon reforming system according to any one of embodiments 1-14, wherein the primary aromatic hydrocarbon product comprises benzene and the heavy aromatic hydrocarbon product comprises toluene and xylenes.

Embodiment 16

A process for producing aromatic hydrocarbons or a catalytic hydrocarbon reforming system according to any one of embodiments 1-14, wherein the primary aromatic hydrocarbon product comprises benzene and the heavy aromatic hydrocarbon product comprises toluene.

Embodiment 17

A process for producing aromatic hydrocarbons or a catalytic hydrocarbon reforming system according to any one of embodiments 1-14, wherein the primary aromatic hydrocarbon product comprises toluene and the heavy aromatic hydrocarbon product comprises xylenes.

Embodiment 18

A process for producing aromatic hydrocarbons or a catalytic hydrocarbon reforming system according to any one of embodiments 1-17, wherein the inorganic support comprises a crystalline or an amorphous inorganic oxide, or combinations thereof.

Embodiment 19

A process for producing aromatic hydrocarbons or a catalytic hydrocarbon reforming system according to any one of embodiments 1-17, wherein the inorganic support comprises a zeolite, a silica-bound zeolite, a clay mineral, silica, alumina, silica-alumina, aluminum phosphate, a heteropolytungstate, titania, zirconia, magnesia, boria, zinc oxide, mixed oxides thereof, or mixtures thereof.

Embodiment 20

A process for producing aromatic hydrocarbons or a catalytic hydrocarbon reforming system according to any one of embodiments 1-17, wherein the inorganic support comprises a zeolite.

Embodiment 21

A process for producing aromatic hydrocarbons or a catalytic hydrocarbon reforming system according to any one of embodiments 1-17, wherein the inorganic support comprises a silica-bound zeolite.

Embodiment 22

A process for producing aromatic hydrocarbons or a catalytic hydrocarbon reforming system according to any one of embodiments 1-17, wherein the inorganic support comprises L-zeolite, X-zeolite, Y-zeolite, omega zeolite, beta zeolite, ZSM-4, ZSM-5, ZSM-10, ZSM-11, ZSM-12, ZSM-20, REY, USY, RE-USY, LZ-210, LZ-210-A, LZ-210-M, LZ-210-T, SSZ-24, SSZ-26, SSZ-31, SSZ-33, SSZ-35, SSZ-37, SSZ-41, SSZ-42, SSZ-44, MCM-58, mordenite, mazzite, faujasite, or combinations thereof.

Embodiment 23

A process for producing aromatic hydrocarbons or a catalytic hydrocarbon reforming system according to any one of embodiments 1-17, wherein the inorganic support comprises L-zeolite, Y-zeolite, ZSM-5, mordenite, omega zeolite, or beta zeolite.

Embodiment 24

A process for producing aromatic hydrocarbons or a catalytic hydrocarbon reforming system according to any one of embodiments 1-23, wherein the catalyst comprises a Group 8-10 metal selected independently from ruthenium, rhodium, palladium, osmium, iridium, platinum, or any combination thereof.

Embodiment 25

A process for producing aromatic hydrocarbons or a catalytic hydrocarbon reforming system according to any one of embodiments 1-23, wherein the catalyst comprises at least one Group 8 metal selected from iron, ruthenium, osmium, or combinations thereof.

Embodiment 26

A process for producing aromatic hydrocarbons or a catalytic hydrocarbon reforming system according to any one of embodiments 1-23, wherein the catalyst comprises at least one Group 9 metal selected from cobalt, rhodium, iridium, or combinations thereof.

Embodiment 27

A process for producing aromatic hydrocarbons or a catalytic hydrocarbon reforming system according to any one of embodiments 1-23, wherein the catalyst comprises at least one Group 10 metal selected from nickel, palladium, platinum, or combinations thereof.

Embodiment 28

A process for producing aromatic hydrocarbons or a catalytic hydrocarbon reforming system according to any one of embodiments 1-23, wherein the catalyst comprises platinum and a zeolite.

Embodiment 29

A process for producing aromatic hydrocarbons or a catalytic hydrocarbon reforming system according to any one of embodiments 1-23, wherein the catalyst comprises platinum and L-zeolite.

Embodiment 30

A process for producing aromatic hydrocarbons or a catalytic hydrocarbon reforming system according to any one of embodiments 1-29, wherein the halide comprises fluoride, chloride, bromide, iodide, or combinations thereof.

Embodiment 31

A process for producing aromatic hydrocarbons or a catalytic hydrocarbon reforming system according to any one of embodiments 1-29, wherein the halide comprises fluoride, chloride, or a combination thereof.

Embodiment 32

A process for producing aromatic hydrocarbons or a catalytic hydrocarbon reforming system according to any one of embodiments 1-29, wherein the halide comprises fluoride.

Embodiment 33

A process for producing aromatic hydrocarbons or a catalytic hydrocarbon reforming system according to any one of embodiments 1-29, wherein the halide comprises chloride.

Embodiment 34

A process for producing aromatic hydrocarbons or a catalytic hydrocarbon reforming system according to any one of embodiments 1-33, wherein the total halide concentration is up to 5 wt % relative to the weight of the catalyst prior to reduction.

Embodiment 35

A process for producing aromatic hydrocarbons according to embodiments 1 and 3-34, further comprising analyzing the composition of the reactor effluent stream and the reactant feed stream and operating the process to maintain or achieve a desired heptane to toluene mole ratio of from about 1:10 to about 20:1.

Embodiment 36

A process for producing aromatic hydrocarbons according to embodiment 10, wherein the reactant feed stream has a higher heat capacity than the reactor feedstock.

Embodiment 37

A process for producing aromatic hydrocarbons according to embodiments 1 and 3-36, further comprising the step of separating the product stream into a primary ($C_6$) aromatic hydrocarbon product and a heavy aromatic hydrocarbon product.

Embodiment 38

A process for producing aromatic hydrocarbons according to embodiment 37, further comprising the step of returning the heavy aromatic hydrocarbon product to the diluent input line for addition to the reactor feedstock.

Embodiment 39

A process for producing aromatic hydrocarbons according to embodiment 38, further comprising the step of returning the heavy aromatic hydrocarbon product to the diluent input line for addition to the reactor feedstock, wherein the first temperature is within from about 10° F. to about 90° F. of the second temperature.

Embodiment 40

A process for producing aromatic hydrocarbons according to Embodiment 36 wherein a total heat duty required by the at least one furnace is reduced by about 5%, 10%, 15%, 20%, 25%, 30%, 35%, 40%, 50%, 55%, or 60% when the reactant feed stream has a higher heat capacity compared to the heat capacity of the reactor feedstock.

Embodiment 41

A process for producing aromatic hydrocarbons according to embodiment 39, further comprising the step of returning the heavy aromatic hydrocarbon product to the diluent input line for addition to the reactor feedstock, wherein the first temperature plus the second temperature divided by two can be lower than when the high heat capacity heavy aromatic hydrocarbon product is not recycled, and still provide the same level of conversion as when the heavy aromatic hydrocarbon product is not recycled, wherein the conversion is at least 60% on a molar basis.

Embodiment 42

A process for producing aromatic hydrocarbons according to embodiment 35, further comprising the step of returning the raffinate to the fractionator inlet.

Embodiment 43

A process for producing aromatic hydrocarbons according to embodiment 35, further comprising the steps of returning the heavy aromatic hydrocarbon product to the diluent input line and returning the raffinate to the fractionator inlet.

Embodiment 44

A process for reforming hydrocarbons according to any one of embodiments 1, 3-34 and 35-43, wherein the conditions for aromatizing at least a portion of the aliphatic hydrocarbons comprise catalyst startup at a gas flow rate comprising a GHSV of between 400 $hr^{-1}$ and 2000 $hr^{-1}$ and a heat-up rate of between 5° F./hr and 50° F./hr during catalyst reduction above about 500° F., wherein the catalyst comprises a halided zeolite catalyst.

Embodiment 45

A process for reforming hydrocarbons according to any one of embodiments 1, 3-34 and 35-44, wherein the conditions for aromatizing at least a portion of the aliphatic hydrocarbons comprise catalyst startup at a gas flow rate comprising a GHSV of between 600 $hr^{-1}$ and 1500 $hr^{-1}$ and a heat-up rate of between 10° F./hr and 30° F./hr during catalyst reduction above about 500° F., wherein the catalyst comprises a fluorided zeolite platinum catalyst.

Embodiment 46

A process for reforming hydrocarbons according to any one of embodiments 1, 3-34 and 35-45, wherein the conditions for aromatizing at least a portion of the aliphatic hydrocarbons comprise catalyst startup at a gas flow rate comprising a GHSV of between 600 $hr^{-1}$ and 1500 $hr^{-1}$ and a heat-up rate of between 10° F./hr and 25° F./hr during catalyst reduction above about 500° F., wherein the catalyst comprises a fluorided-chlorided zeolite platinum catalyst.

Embodiment 47

A process for reforming hydrocarbons according to any one of embodiments 1, 3-34 and 35-46, wherein the contacting step occurs in a radial flow reactor.

Embodiment 48

A process for reforming hydrocarbons according to any one of embodiments 1, 3-34 and 35-47, further comprising the step of removing impurities from the reactor feedstock, prior to the addition of the diluent.

Embodiment 49

A process for reforming hydrocarbons according to any one of embodiments 1, 3-34 and 35-48, further comprising the step of passing the reactor feedstock through a sulfur removal system prior to the addition of the diluent.

Embodiment 50

A process for reforming hydrocarbons according to any one of embodiments 1, 3-34 and 35-49, further comprising the step of passing the reactor feedstock through a sulfur converter-absorber prior to the addition of the diluent.

Embodiment 51

A process for reforming hydrocarbons according to any one of embodiments 1, 3-34 and 35-50, further comprising the step of adding an oxygenate or a nitrogenate to the reactor feedstock.

Embodiment 52

A process for reforming hydrocarbons according to any one of embodiments 1, 3-34 and 35-51, wherein the steps are repeated in one or more subsequent reactors in series.

Embodiment 53

A catalytic hydrocarbon reforming system according to embodiments 2 and 3-52, further comprising a second return line extending from the separation system, wherein the second return line is configured to provide raffinate to the fractionator inlet.

Embodiment 54

A catalytic hydrocarbon reforming system according to embodiments 2 and 3-52, further comprising a third return line extending from the separation system, wherein the third return line is configured to provide hydrogen to the reactant feed stream.

Embodiment 55

A catalytic hydrocarbon reforming system according to embodiments 2 and 3-53, further comprising a third return line extending from the separation system, wherein the third return line is configured to first provide hydrogen to a dryer and is configured to subsequently provide the dried hydrogen to the reactant feed stream.

Embodiment 56

A catalytic hydrocarbon reforming system according to embodiments 2 and 3-54, further comprising a sulfur converter-absorber between the fractionator and the diluent input line.

Embodiment 57

A catalytic hydrocarbon reforming system according to embodiments 2 and 3-56, wherein the system is absent a recycle line compressor.

What is claimed is:
1. A catalytic hydrocarbon reforming system comprising:
a fractionator having an inlet to receive an initial feedstock comprising naphtha and an outlet to discharge a reactor feedstock comprising aliphatic hydrocarbons;
a diluent input line for adding a diluent comprising a heavy aromatic hydrocarbon to the reactor feedstock to form a reactant feed stream having a first temperature;
at least one furnace capable of heating the reactant feed stream to a second temperature;
at least one reactor charged with a catalyst comprising an inorganic support, a Group 8-10 metal, and at least one halide, the reactor having an inlet to receive the reactant feed stream and an outlet to discharge a reactor effluent stream at a third temperature; the reactor effluent stream comprising a primary aromatic hydrocarbon product and a heavy aromatic hydrocarbon product;

a separation system that receives the reactor effluent stream and separately discharges the primary aromatic hydrocarbon product, the heavy aromatic hydrocarbon product, hydrogen, and a raffinate; and a first return line extending from the separation system to the diluent input line for providing the diluent, the diluent comprising at least a portion of the heavy aromatic hydrocarbon product.

2. A catalytic hydrocarbon reforming system according to claim 1, wherein the reactor feedstock and the reactant feed stream comprise $C_6$ to $C_8$ aliphatic hydrocarbons.

3. A catalytic hydrocarbon system according to claim 1, wherein the reactor feedstock and the reactant feed stream comprise light naphtha.

4. A catalytic hydrocarbon reforming system according to claim 1, wherein the primary aromatic hydrocarbon product comprises benzene and the heavy aromatic hydrocarbon product comprises toluene and xylenes.

5. A catalytic hydrocarbon reforming system according to claim 1, further comprising a second return line extending from the separation system, wherein the second return line is configured to provide the raffinate to the fractionator inlet.

6. A catalytic hydrocarbon reforming system according to claim 1, further comprising a third return line extending from the separation system, wherein the third return is configured to provide hydrogen to the reactant feed stream.

7. A catalytic hydrocarbon reforming system according to claim 1, further comprising a third return line extending from the separation system, wherein the third return line is configured to first provide hydrogen to a dryer and is configured to subsequently provide the dried hydrogen to the reactant feed stream.

8. A catalytic hydrocarbon reforming system according to claim 1, further comprising a sulfur converter-absorber between the fractionator and the diluent input line.

9. A catalytic hydrocarbon reforming system according to claim 1, wherein the system is absent a recycle line compressor.

10. A catalytic hydrocarbon reforming system according to claim 1, wherein the first temperature is within from about 10° F. to about 90° F. from the second temperature.

11. A catalytic hydrocarbon reforming system according to claim 1, wherein the reactant feed stream has a higher heat capacity than the reactor feedstock.

12. A catalytic hydrocarbon reforming system according to claim 11, wherein the system is configured so that the heat duty provided by the furnace to the reactor feed stream is reduced by at least 5% as compared to the heat duty provided when the reactant feed stream does not have a higher heat capacity than the reactor feedstock.

13. A catalytic hydrocarbon reforming system according to claim 1, wherein the reactor is a radial flow reactor.

14. A catalytic hydrocarbon reforming system according to claim 1, wherein the inorganic support comprises a zeolite, a silica-bound zeolite, a clay mineral, silica, alumina, silica-alumina, aluminum phosphate, a heteropolytungstate, titania, zirconia, magnesia, boria, zinc oxide, mixed oxides thereof, or mixtures thereof.

15. A catalytic hydrocarbon reforming system according to claim 1, wherein the inorganic support comprises L-zeolite, X-zeolite, Y-zeolite, omega zeolite, beta zeolite, ZSM-4, ZSM-5, ZSM-10, ZSM-11, ZSM-12, ZSM-20, REY, USY, RE-USY, LZ-210, LZ-210-A, LZ-210-M, LZ-210-T, SSZ-24, SSZ-26, SSZ-31, SSZ-33, SSZ-35, SSZ-37, SSZ-41, SSZ-42, SSZ-44, MCM-58, mordenite, mazzite, faujasite, or combinations thereof.

16. A catalytic hydrocarbon reforming system according to claim 1, wherein the catalyst comprises a Group 8-10 metal selected independently from ruthenium, rhodium, palladium, osmium, iridium, platinum, or any combination thereof.

17. A catalytic hydrocarbon reforming system according to claim 1, wherein the halide comprises fluoride, chloride, or a combination thereof.

18. A catalytic hydrocarbon reforming system according to claim 1, wherein the system further comprises a purifier configured to remove one or more impurities from the reactor feedstock to form a purified reactor feedstock stream, and wherein the diluent input line is configured to add the diluent to the purified reactor feedstock stream to form the reactant feed stream.

19. A catalytic hydrocarbon reforming system according to claim 18, wherein the purifier is a sulfur removal system.

20. A catalytic hydrocarbon reforming system according to claim 19, wherein the purifier is a sulfur converter-absorber.

\* \* \* \* \*